United States Patent
Fujiwara et al.

(10) Patent No.: US 10,668,281 B2
(45) Date of Patent: Jun. 2, 2020

(54) SPINAL CORD STIMULATION DEVICE FOR GAIT TRAINING

(71) Applicants: TOKAI UNIVERSITY EDUCATIONAL SYSTEM, Tokyo (JP); KEIO UNIVERSITY, Tokyo (JP)

(72) Inventors: Toshiyuki Fujiwara, Isehara (JP); Yoshihisa Masakado, Isehara (JP); Junichi Ushiba, Yokohama (JP)

(73) Assignees: Tokai University Educational System, Tokyo (JP); Keio University, Tokyo (JP)

( * ) Notice: Subject to any disclaimer, the term of this patent is extended or adjusted under 35 U.S.C. 154(b) by 153 days.

(21) Appl. No.: 15/558,171

(22) PCT Filed: Mar. 14, 2016

(86) PCT No.: PCT/JP2016/001413
§ 371 (c)(1),
(2) Date: Sep. 13, 2017

(87) PCT Pub. No.: WO2016/147643
PCT Pub. Date: Sep. 22, 2016

(65) Prior Publication Data
US 2018/0071528 A1 Mar. 15, 2018

(30) Foreign Application Priority Data
Mar. 13, 2015 (JP) .................................. 2015-051122

(51) Int. Cl.
*A61N 1/18* (2006.01)
*A61N 1/36* (2006.01)
(Continued)

(52) U.S. Cl.
CPC ........... *A61N 1/36003* (2013.01); *A61H 1/02* (2013.01); *A61N 1/0452* (2013.01);
(Continued)

(58) Field of Classification Search
CPC .................... A61N 1/36003; A61N 1/36017
See application file for complete search history.

(56) References Cited

U.S. PATENT DOCUMENTS 7,403,821 B2 * 7/2008 Haugland .......... A61B 5/04001
607/48
7,949,403 B2 * 5/2011 Palermo ............... A61N 1/0452
607/46
(Continued)

FOREIGN PATENT DOCUMENTS

CN 104220128 A 12/2014
JP 2014-514043 A 6/2014
(Continued)

*Primary Examiner* — Michael J D Abreu
(74) *Attorney, Agent, or Firm* — Knobbe, Martens, Olson & Bear, LLP

(57) ABSTRACT

In order to make advanced gait training easy and effective, an electrical spinal cord stimulator for gait training used in gait training for those who have difficulty in walking due to hemiplegia includes: first and second electrodes attached to a rehabilitant; a detector which detects a gait-related physical movement of the rehabilitant; and an electrical sensory nerve stimulation generator which generates, according to a detection result of the detector, electrical stimulation to be applied through the first and second electrodes to a nerve root of a sensory nerve which communicates with a spinal cord.

5 Claims, 3 Drawing Sheets

(51) Int. Cl.
- *A61H 1/02* (2006.01)
- *A61N 1/04* (2006.01)
- *A61B 5/0476* (2006.01)
- *A61B 5/0488* (2006.01)
- *A61B 5/107* (2006.01)
- *A61B 5/11* (2006.01)
- *A61B 5/00* (2006.01)

(52) U.S. Cl.
CPC ............ *A61N 1/0456* (2013.01); *A61N 1/36* (2013.01); *A61N 1/36014* (2013.01); *A61N 1/36031* (2017.08); *A61B 5/0476* (2013.01); *A61B 5/0488* (2013.01); *A61B 5/1071* (2013.01); *A61B 5/112* (2013.01); *A61B 5/4836* (2013.01)

(56) References Cited

U.S. PATENT DOCUMENTS

| | | |
|---|---|---|
| 2012/0059432 A1 | 3/2012 | Emborg et al. |
| 2013/0123568 A1* | 5/2013 | Hamilton ........... A61N 1/36003 600/13 |
| 2014/0031648 A1 | 1/2014 | Cross |
| 2014/0180361 A1 | 6/2014 | Burdick et al. |
| 2014/0316484 A1 | 10/2014 | Edgerton et al. |
| 2015/0231396 A1 | 8/2015 | Burdick et al. |
| 2016/0310739 A1 | 10/2016 | Burdick et al. |

FOREIGN PATENT DOCUMENTS

| | | |
|---|---|---|
| JP | 2014-533183 A | 12/2014 |
| WO | 2012/129574 A2 | 9/2012 |
| WO | 2014/136852 A1 | 9/2014 |

\* cited by examiner

SPINAL CORD STIMULATION DEVICE FOR GAIT TRAINING

CROSS-REFERENCE TO RELATED APPLICATIONS

This application is the U.S. National Phase under 35. U.S.C. § 371 of International Application PCT/JP2016/001413, filed Mar. 14, 2016, which claims priority to Japanese Patent Application No. 2015-051122, filed Mar. 13, 2015. The disclosures of the above-described applications are hereby incorporated by reference in their entirety.

TECHNICAL FIELD

The present invention relates to an electrical spinal cord stimulator for gait training used, for example, in gait training for those who have difficulty in walking due to hemiplegia.

BACKGROUND ART

In recent years, the number of cerebral strokes which occurred each year exceeds 110,000, and it is estimated that the number of those who suffer from the cerebral stroke is 1,760,000 each year. Many of them suffer from sequelae, which interferes with their activities of daily living (ADL). About 30% of seniors in need of long-term care is said to be due to experiencing a cerebral stroke. About 20 to 30% of the patients who have hemiplegia after a cerebral stroke remain unable to walk even through rehabilitation after the cerebral stroke. Even if they can walk, the percentage of the patients who can walk outside after the stroke remains at 50% or less because of a high risk of fall due to declined walking speed and instability. In these circumstances, a device for effective gait training has been desired.

Known electrical stimulators which apply electrical stimulation to a rehabilitant in training for improvement of the walking movements of the rehabilitant include an electrical stimulator which applies low-frequency electrical stimulation to individual peripheral nerves and muscles to control a simple joint. However, advanced gait training is difficult to achieve through such control of a simple joint. Control of a simple joint can only be adopted into training for those who have mild palsy.

To address this inconvenience, techniques of generating electrical stimulation of complicated types and patterns to apply it to a rehabilitant have also been suggested (see, e.g., Patent Document 1).

CITATION LIST

Patent Document

PATENT DOCUMENT 1: Japanese Translation of PCT International Application No. 2014-514043

SUMMARY OF THE INVENTION

Technical Problem

However, in gait training using the above-mentioned complicated electrical stimulation, there is a risk that the rehabilitant may fall if, for example, there is a difference in timing of muscle activities during walking. It is thus difficult to spread the use of this technique in rehabilitation sites. That is, it is difficult to adopt this technique into training for those who have severe palsy.

In view of this background, it is an object of the invention to perform advanced gait training in an easy and effective manner.

Solution to the Problem

A first aspect of the invention is directed to an electrical spinal cord stimulator for gait training used in gait training for those who have difficulty in walking due to hemiplegia includes:

first and second electrodes attached to a rehabilitant;
a detector which detects a gait-related physical movement of the rehabilitant; and
an electrical sensory nerve stimulation generator which generates, according to a detection result of the detector, electrical stimulation to be applied through the first and second electrodes to a nerve root of a sensory nerve which communicates with a spinal cord.

This configuration may evoke muscle activities similar to walking by noninvasive and relatively weak electrical stimulation, which helps swinging or standing movements of the lower leg of the palsy side and enhances the effects of the gait training.

A second aspect of the invention is an embodiment of the first aspect. In the second aspect, the first electrode is attached to an area from a lower thoracic spine to an upper lumbar spine of the rehabilitant, and the second electrode is attached to an abdominal area of the rehabilitant.

This configuration may easily evoke muscle activities similar to walking as described above, which may enhance the effects of the gait training.

A third aspect of the invention is an embodiment of the first or second aspect. In the third aspect, the electrical stimulation generated by the electrical sensory nerve stimulation generator is an electric signal of 50 mA or less and 50 Hz or more and 100 Hz or less.

In this configuration, gait training is performed with relatively weak stimulation, which may reduce a burden of the rehabilitant.

A fourth aspect of the invention is an embodiment of any one of the first to third aspects. In the fourth aspect, the detector is configured to detect at least one of a muscle potential of a muscle which moves as the rehabilitant walks, an angle of a joint which moves as the rehabilitant walks, and a brain wave generated as the rehabilitant walks.

This configuration realizes the detection according to the state of the rehabilitant, and therefore allows for flexible training.

A fifth aspect of the invention is an embodiment of the fourth aspect. In the fifth aspect, the detector is configured to detect a muscle potential generated by a muscle activity of the triceps surae muscle or the tibialis anterior muscle of the rehabilitant.

In this configuration, the detection is easily accomplished, which may improve the reliability of the gait training.

A sixth aspect of the invention is an embodiment of any one of the first to fifth aspects. In the sixth aspect, the stimulator further includes:

a third electrode attached to the rehabilitant; and
an electrical motor nerve stimulation generator which generates, according to a detection result of the detector, electrical stimulation to be applied to a motor nerve through the third electrode.

This configuration electrically stimulates the extensor of the hip joint in the stance phase, and may further facilitate the gate movements, thereby making it possible to further enhance the effects of the training.

A seventh aspect of the invention is an embodiment of the sixth aspect. In the seventh aspect, the electrical stimulation generated by the electrical motor nerve stimulation generator is an electric signal of 50 mA or less and 30 Hz or less.

This configuration may further enhance the effects of the training.

An eighth aspect of the invention is an embodiment of the seventh aspect. In the eighth aspect, the electrical stimulation generated by the electrical motor nerve stimulation generator is applied to buttocks of the rehabilitant.

This configuration may further enhance the effects of the training.

A ninth aspect of the invention is an embodiment of any one of the first to eighth aspects. In the ninth aspect, at least one of the electrical sensory nerve stimulation generator or the electrical motor nerve stimulation generator is configured such that delay time from when the physical movement of the rehabilitant is detected by the detector to when the electrical stimulation is generated is adjustable.

This configuration may provide training depending on the state of the rehabilitant, which may enhance the effects of the training for individual cases.

Advantages of the Invention

According to the present invention, it is possible to perform advanced gait training in an easy and effective manner.

DETAILED DESCRIPTION

An embodiment of the present invention will be described in detail below, with reference to the drawings.

(Configuration of Electrical Spinal Cord Stimulator for Gait Training)

Figure 1:
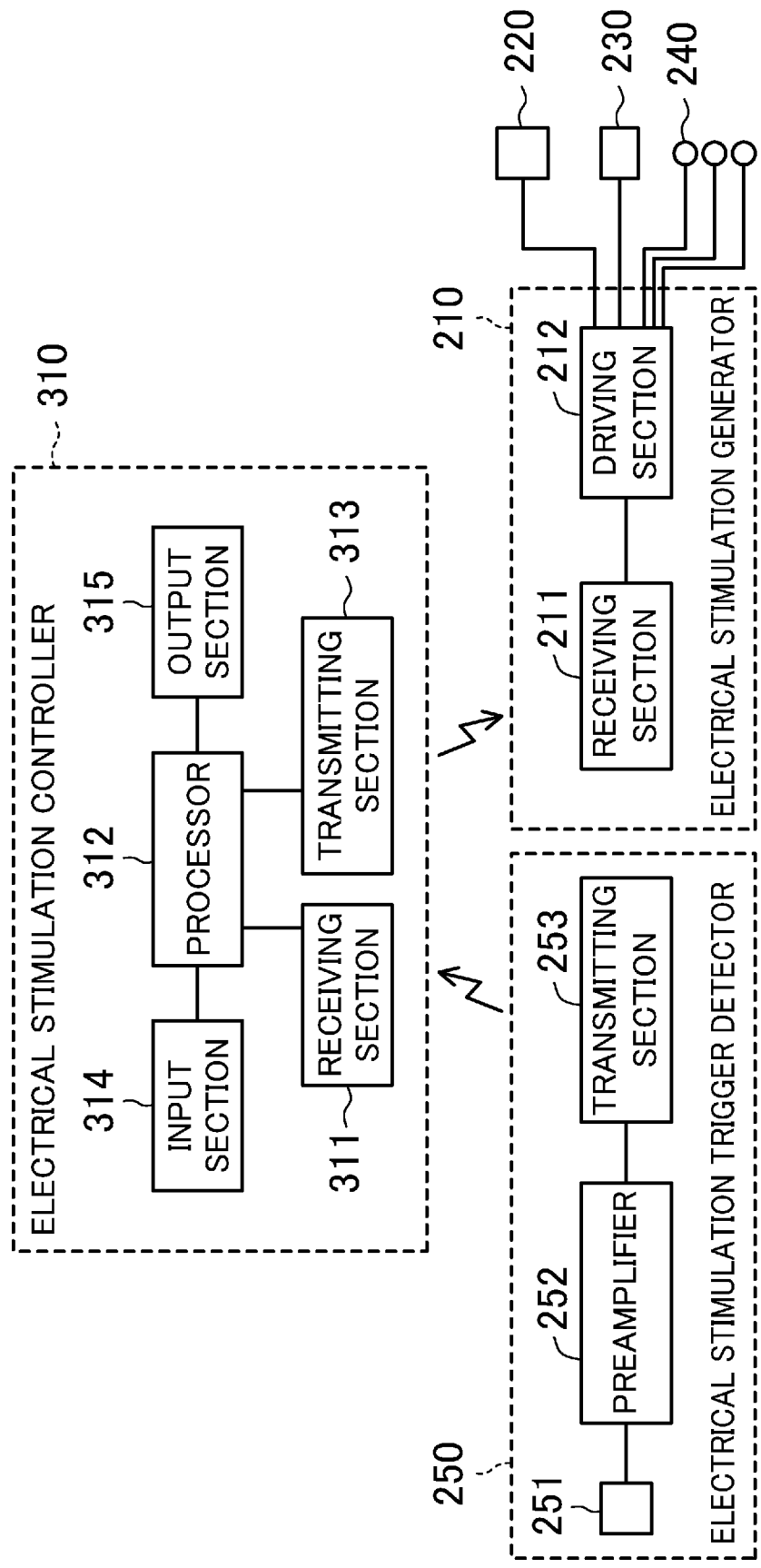
FIG. 1 is a block diagram illustrating a circuit configuration of an electrical spinal cord stimulator for gait training.
Figure 2:
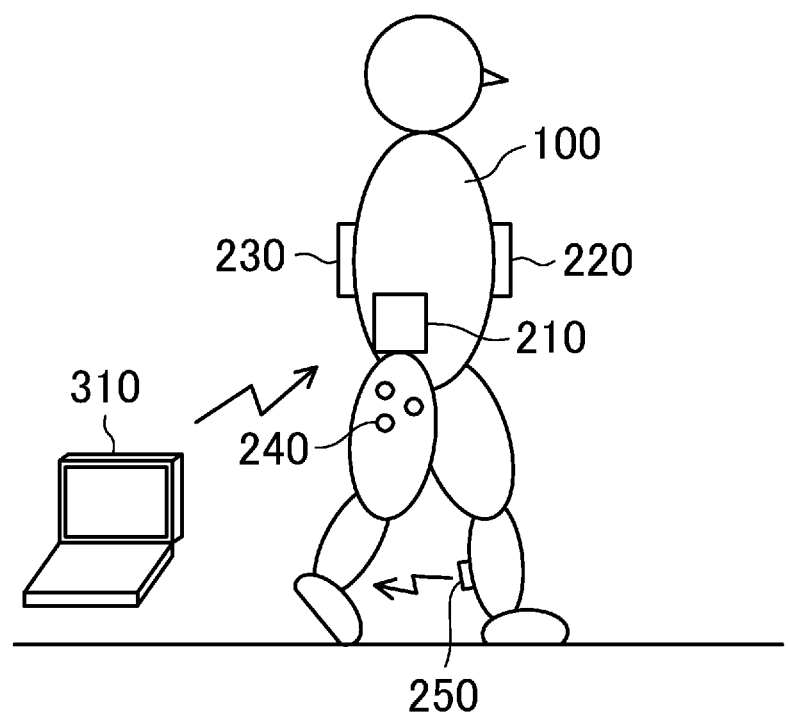
FIG. 2 is a diagram illustrating an example state of use of the electrical spinal cord stimulator for gait training.
Figure 3:
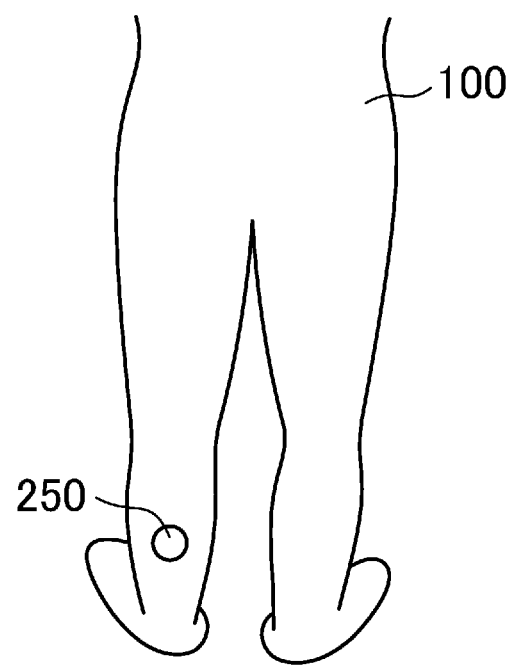
FIG. 3 is a diagram illustrating an example state of attachment of an electrical stimulation trigger detector 250.
Figure 4:
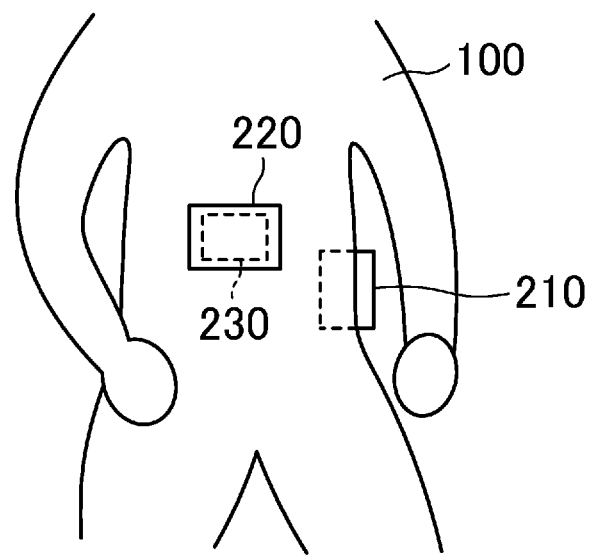
FIG. 4 is a diagram illustrating an example state of attachment of an abdominal electrode 220 and a dorsal electrode 230.
Figure 5:
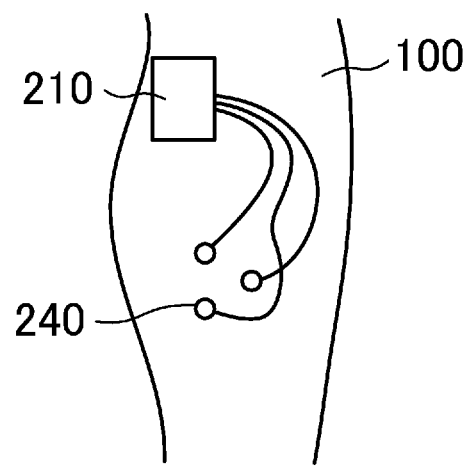
FIG. 5 is a diagram illustrating an example state of attachment of a buttock electrode 240.

The electrical spinal cord stimulator for gait training of an embodiment of the present invention is comprised of an electrical stimulation trigger detector 250, an electrical stimulation controller 310, and an electrical stimulation generator 210, as illustrated in FIG. 1. The electrical stimulation trigger detector 250 is attached, for example, to a lower leg of a non-palsy side of a rehabilitant 100 as illustrated in FIGS. 2 and 3. The electrical stimulation generator 210 is secured, for example, to a lumbar region of the rehabilitant 100 with a belt or the like as illustrated in FIGS. 2, 4 and 5. The electrical stimulation controller 310 is placed near the rehabilitant 100.

The electrical stimulation trigger detector 250 includes a muscle potential detector electrode 251 which detects a muscle potential, a preamplifier 252 which amplifies the muscle potential detected, and a transmitting section 253 which transmits an amplified signal by radio waves. The electrical stimulation trigger detector 250 detects muscle activities of, e.g., the triceps surae muscle or tibialis anterior muscle of the non-palsy side of the rehabilitant 100.

The electrical stimulation controller 310 includes a receiving section 311 which receives the radio waves from the electrical stimulation trigger detector 250, a processor 312 which generates an electrical stimulation instruction signal based on the received signal, and a transmitting section 313 which transmits the electrical stimulation instruction signal by radio waves. The electrical stimulation controller 310 further includes an input section 314 and an output section 315. Predetermined setting values are input in the input section 314, such as determination threshold values for the muscle activities, delay time in generating an electrical stimulation signal, and intensity of the stimulation such as a frequency and a current of the electrical stimulation signal. The output section 315 is used to monitor the state of behavior of the electrical stimulation controller 310. The electrical stimulation controller 310 outputs the electrical stimulation instruction signal to the electrical stimulation generator 210 when the amplitude of the muscle potential detected by the electrical stimulation trigger detector 250 is greater or equal to a predetermined threshold value entered into the input section 314.

The electrical stimulation generator 210 includes a receiving section 211 which receives the radio wave transmitted from the electrical stimulation controller 310 and a driving section 212 which generates, for example, a first electrical stimulation signal of 50 mA or less and 50 Hz or more and 100 Hz or less and a second electrical stimulation signal of 50 mA or less and 30 Hz or less. The first electrical stimulation signal is output to the abdominal electrode 220 (e.g., a negative electrode) and the dorsal electrode 230 (e.g., a positive electrode). As illustrated in FIG. 4, the abdominal electrode 220 is attached to an abdominal area of the rehabilitant 100 as a surface electrode, whereas the dorsal electrode 230 is attached to an area from a lower thoracic spine to an upper lumbar spine of the rehabilitant 100 as a surface electrode, so that first electrical stimulation is given to the nerve root of the sensory nerve which communicates with the spinal cord. The second electrical stimulation signal is output to a buttock electrode 240 (e.g., a positive electrode and a negative electrode, and if necessary, another electrode for detecting a muscle potential). The buttock electrode 240 is attached to the buttocks of the rehabilitant 100 as a surface electrode as illustrated in FIG. 5, so that second electrical stimulation is given to an extensor of a hip joint.

(Example Operation)

Gait training using the above-described electrical spinal cord stimulator for gait training is conducted in the following manner.

When the triceps surae muscle or the tibialis anterior muscle of the non-palsy side of the rehabilitant 100 moves, a signal corresponding to the muscle potential associated with this movement is transmitted from the electrical stimulation trigger detector 250 to the electrical stimulation controller 310. If the amplitude of the muscle potential detected is greater or equal to a predetermined value, the electrical stimulation controller 310 transmits the electrical stimulation instruction signal to the electrical stimulation generator 210. The electrical stimulation generator 210 outputs the first electrical stimulation signal to the abdominal electrode 220 and the dorsal electrode 230 and the second electrical stimulation signal to the buttock electrode 240, according to the electrical stimulation instruction signal.

With the abdominal electrode 220 being attached to the abdominal area of the rehabilitant 100, and the dorsal electrode 230 being attached to the area from the lower thoracic spine to the upper lumbar spine, as described above, the high-frequency stimulation applied to the nerve roots of the spinal cord is realized, by the first electrical stimulation, as percutaneous and noninvasive stimulation of the sensory nerve. That is, a muscle activity similar to walking is evoked, due to a spinal reflex, by the electrical stimulation applied to the lower thoracic spinal cord, which reconstructs a lower leg movement pattern required for walking and helps a swinging or standing movement of the lower leg of the palsy side. Further, the gait movement is further facilitated with the buttock electrode 240 attached to the buttocks of the rehabilitant 100, and the second electrical stimulation applied to the extensor of the hip joint in a stance phase. This configuration therefore allows the rehabilitant 100 with severe to moderate palsy to have effective gait training.

The above-described sensory nerve stimulation at the nerve roots of the spinal cord makes it possible, unlike stimulation of individual peripheral nerves and muscles, to support a series of physiological gait movements, that is, to stimulate movements of multiple joints, in which leg movements, such as those in the swing, push-off, and stance phases in the gait movement, may be reconstructed. Moreover, the intensity of such stimulation may be weaker than the intensity of stimulation applied directly to motor nerves.

Stimulating a spinal reflex arc necessary for walking at appropriate timing during walking facilitates the physiological gate movements by the spinal cord stimulation. Further, stimulating the spinal reflex arc, in combination with the electrical stimulation to a hip joint extensor group intended for the extension of the hip joint which triggers the gait movements, may strengthen the neural circuits necessary for walking. Consequently, the rehabilitant 100 with walking disability due to palsy may have improved gait functions.

Specifically, for example, improvement about reciprocal inhibition via the spinal cord was observed in a cerebral stroke patient who was in a chronic phase two years or more after the stroke and received, as a rehabilitant 100, the above-described rehabilitation training (five times in total). In addition, 10 meter gait speed improved from fifteen to twelve seconds. The effect of the rehabilitation training continued up to six months from the completion of the training.

It is easy to use the above-described device in medical rehabilitation sites, for the above-described device is small in size and lightweight and the electrical stimulator does not cause pain due to its weak intensity of stimulation which is about twice a sensitivity threshold and percutaneous stimulation. Since electrical stimulation itself is often used in rehabilitation sites, trainers or those who handle the device can easily use it.

Moreover, the stimulator may be attached within ten minutes or so by attaching the electrodes and electromyogram electrodes, too, with adhesive stickers. The above-described electrical stimulator may be used in ordinary gait training without an additional oversize device, and may thus be used in a rehabilitation training room.

(Variations)

In the above description, an example in which the muscle activities of the triceps surae muscle and the tibialis anterior muscle of the non-palsy side are detected as a trigger of electrical stimulation, has been described, but this is a non-limiting example. Various changes related to the gait timing of the rehabilitant 100 may be used as a trigger. Specifically, muscle potentials of another muscle which moves as the rehabilitant walks, an angle of a joint which moves as the rehabilitant walks, and brain waves generated as the rehabilitant walks may be detected, for example.

Moreover, a plurality of these parameters may be combined to improve detection accuracy and reliability.

Further, the delay time may be adjustable for each rehabilitant 100 and/or according to the progress of the gait training or other factors by making it possible to enter various delay time from when the changes related to the movement of the rehabilitant 100, such as those described above, are detected to when electrical sensory nerve stimulation and/or electrical motor nerve stimulation is applied.

In the above description, an example in which the electrical stimulation trigger detector 250, the electrical stimulation controller 310, and the electrical stimulation generator 210 transmit and receive signals by radio communication has been described, but this is a non-limiting example. For example, these elements may be wire-connected to one another, or may be configured as a single unit to which a sensor and/or an electrode is connected. In such a case, a signal for monitoring a status of the electrical stimulation application may be transmitted wirelessly to a device or the like which monitors, analyzes, and records the gait training.

DESCRIPTION OF REFERENCE CHARACTERS

100 Rehabilitant
210 Electrical Stimulation Generator
211 Receiving Section
212 Driving Section
220 Abdominal Electrode
230 Dorsal Electrode
240 Buttock Electrode
250 Electrical Stimulation Trigger Detector
251 Muscle Potential Detection Electrode
252 Preamplifier
253 Transmitting Section
310 Electrical Stimulation Controller
311 Receiving Section
312 Processor
313 Transmitting Section
314 Input Section
315 Output Section

What is claimed is:

1. An electrical spinal cord stimulator for gait training used in gait training for those who have difficulty in walking due to hemiplegia, the stimulator comprising:
    first and second electrodes attached to a rehabilitant;
    a detector which detects a gait-related physical movement of the rehabilitant; and
    an electrical sensory nerve stimulation generator which generates, according to a detection result of the detector, electrical stimulation to be applied through the first and second electrodes to a nerve root of a sensory nerve which communicates with a spinal cord;
    wherein
    the first electrode is attached to an area from a lower thoracic spine to an upper lumbar spine of the rehabilitant, and
    the second electrode is attached to an abdominal area of the rehabilitant;
    wherein
    the electrical stimulation generated by the electrical sensory nerve stimulation generator is an electric signal of 50 mA or less and 50 Hz or more and 100 Hz or less; and
    further comprising:
    a third electrode attached to the rehabilitant; and
    an electrical motor nerve stimulation generator which generates, according to the detection result of the detector, electrical stimulation to be applied to a motor nerve through the third electrode;

wherein the electrical stimulation generated by the electrical motor nerve stimulation generator and applied by the first and second electrodes is an electric signal of 50 mA or less and 30 Hz or less:

wherein the electrical stimulation generated by the electrical motor nerve stimulation generator is applied to buttocks of the rehabilitant by the third electrode.

2. The stimulator of claim 1, wherein the detector is configured to detect at least one of a muscle potential of a muscle which moves as the rehabilitant walks, an angle of a joint which moves as the rehabilitant walks, and a brain wave generated as the rehabilitant walks.

3. The stimulator of claim 2, wherein the detector is configured to detect a muscle potential generated by a muscle activity of the triceps surae muscle or the tibialis anterior muscle of the rehabilitant.

4. The stimulator of claim 1, wherein at least one of the electrical sensory nerve stimulation generator or the electrical motor nerve stimulation generator is configured such that delay time from when the physical movement of the rehabilitant is detected by the detector to when the electrical stimulation is generated is adjustable.

5. The stimulator of claim 1, wherein the first electrode is attached to an dorsal area of the rehabilitate and configured to cover an area from a lower thoracic spine to an upper lumbar spine of the rehabilitant, and the second electrode is attached to an abdominal area of the rehabilitant.

* * * * *